United States Patent
Casares et al.

(10) Patent No.: US 9,557,323 B2
(45) Date of Patent: Jan. 31, 2017

(54) HUMANIZED TRANSGENIC MOUSE MODEL

(75) Inventors: Sofia A. Casares, Potomac, MD (US); Teodor D. Brumeanu, Potomac, MD (US); Thomas L. Richie, Glenelg, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/581,483

(22) PCT Filed: Sep. 26, 2011

(86) PCT No.: PCT/US2011/001656
§ 371 (c)(1),
(2), (4) Date: Apr. 26, 2013

(87) PCT Pub. No.: WO2012/039779
PCT Pub. Date: Mar. 29, 2012

(65) Prior Publication Data
US 2013/0217043 A1    Aug. 22, 2013

Related U.S. Application Data (60) Provisional application No. 61/386,118, filed on Sep. 24, 2010.

(51) Int. Cl.
*A01K 67/027*     (2006.01)
*G01N 33/50*      (2006.01)
*A61D 19/04*      (2006.01)

(52) U.S. Cl.
CPC ....... *G01N 33/5088* (2013.01); *A01K 67/0278* (2013.01); *A61D 19/04* (2013.01); *A01K 2217/052* (2013.01); *A01K 2217/15* (2013.01); *A01K 2227/105* (2013.01); *A01K 2267/03* (2013.01)

(58) Field of Classification Search
CPC ............... A01K 67/0278; A01K 2227/105; G01N 33/5088; A61D 19/04
See application file for complete search history.

(56) References Cited

U.S. PATENT DOCUMENTS

| | | |
|---|---|---|
| 2001/0044937 A1 | 11/2001 | Schatten |
| 2007/0209083 A1* | 9/2007 | Thiam et al. ............ 800/14 |
| 2009/0226893 A1 | 9/2009 | Baker |

OTHER PUBLICATIONS

Watanab et al International Immunology, 2009, vol. 21, No. 7, pp. 843-858.*
Wanlanabe el at PNAS, International Immunology, 2009, 21(7), 843-858.*
Ito et al J. Exp. Med. 1996, 183, 2635-2644.*
Shultz PNAS, Jul. 20, 2010, 107, 29, 13022-13027.*
Jaiswal et al PLos One, 2009, vol. 4, Issue 10, e7251, pp. 1-12.*
Pearson et al Clin Exp Immunol. Nov. 2008; 154(2): 270-284).*
Guerder et al The Journal of Immunology, 1998, 161: 2128-2140.*
Ishikawa et al. Blood 106: 1565-1573, 2005.*
Wantanabe, et al. The analysis of the functions of human B and T cells in humanized NOD/shi-scid/gcnull (NOG) mice (hu-HSC NOG mice). International Immunology. 2009, vol. 21, No. 7, pp. 843-858. esp: abstract, p. 854 first column; p. 844, section entitled "Mice and reconstitution with human stem cells", p. 857 first column, first complete paragraph; p. 855 first sentence; p. 848 section entitled "IgG response of the human B cells from hu_HSC NOG mice to in vitro stimulation"; p. 854 section entitled "Conclusions"; Fig 1 (relevant to claims 1-12).
Ito, et al. HLA-DR4-IE Chimeric Class II Transgenic, Murine Class II-Deficient Mice Are Susceptible to Experimental Allergic Encephalomyelitis. J. Exp. Med. Jun. 1, 1996, vol. 183, p. 2635-2644. esp: abstract, p. 2636 sections entitled "Gene Constructs of HLA-DRA-IED-alpha and HLA-DRB1*0401-IED- beta" and "Transgenic mice". (relevant to claim 4).
Danner, et al. Expression of HLA Class II Molecules in Humanized NOD.Rag1KO.1L2RgcKO Mice is Critical for Development and Function of Human T and B Cells. PLoS One. May 17, 2001, vol. 6(5): e19826. published May 17, 2011 entire document. (relevant to claims 1-5).

* cited by examiner

*Primary Examiner* — Anoop Singh
(74) *Attorney, Agent, or Firm* — Ning Yang; Diane P. Tso; Albert M. Churilla (57) ABSTRACT

Provided is a transgenic animal model for testing immunogenicity and protective efficacy of human vaccines and the method for generating such a multitransgenic animal. Also disclosed are methods for screening compositions for human vaccine development. More specifically, a mouse model capable of expressing human leukocyte antigen DR4, and human costimulatory molecules (CD80) upon infusion of human HLA-matched hematopoietic stem cells, which can develop into a functional human immune system is provided.

2 Claims, 10 Drawing Sheets

Development of human B cells and immunoglobulins by DRAG mice

A) Percentage of human B cell reconstituted mice

C) Human IgM in plasma (*) pending analysis

B) Frequency of human B cells in blood

D) Human IgG in plasma

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: HLA-DR4 alpha forward primer

<400> SEQUENCE: 1
aatcctgacc aatcaggcga g                                              21

<210> SEQ ID NO 2
<211> LENGTH: 21
<212> TYPE: DNA
<213> ORGANISM: Artificial Sequence
<220> FEATURE:
<223> OTHER INFORMATION: HLA-DR4alpha Reverse Primer

<400> SEQUENCE: 2
gcggaagagg tgatcgtccc t                                              21

<210> SEQ ID NO 3
<211> LENGTH: 20
<212> TYPE: DNA
<213> ORGANISM: Artificial Sequence
<220> FEATURE:
<223> OTHER INFORMATION: HLA-DR4 beta Forward

<400> SEQUENCE: 3
gtttcttgga gcaggttaaa                                                20

<210> SEQ ID NO 4
<211> LENGTH: 20
<212> TYPE: DNA
<213> ORGANISM: Artificial Sequence
<220> FEATURE:
<223> OTHER INFORMATION: HLA-DR4beta Reverse

<400> SEQUENCE: 4
ctgcactgtg aagctctcac                                                20
```

HUMANIZED TRANSGENIC MOUSE MODEL

CROSS-REFERENCE TO RELATED APPLICATIONS

This application claims priority to U.S. Patent Application No. 61/386,118, filed Sep. 24, 2010.

SEQUENCE LISTING

The information recorded in electronic form submitted under Rule 13ter is identical to the sequence listing as contained in the international application as filed on paper

BACKGROUND

This invention relates to a transgenic animal model for testing immunogenicity and protective efficacy of human vaccines as well as a method for generating such a multi-transgenic animal. This invention also relates to methods for screening compositions for human vaccine development. More specifically, the present invention relates to a mouse model capable of expressing human leukocyte antigen DR4, and human costimulatory molecules (CD80) upon infusion of human HLA-matched hematopoietic stem cells, which reconstitute long-lived and functional human T and B cells.

Human vaccine research often requires in vivo analysis to test the immunogenicity, protective efficacy, and toxicity of certain vaccine candidates. However, in vivo human study is severely limited due to ethical and technical constraints. There is a growing need for an animal model to carry out in vivo studies of human cells, tissues and organs, without putting individuals at risk. Many important studies have been carried out using mice as an animal model in research of complex human biological systems. There is a growing need of "humanized mouse model" capable of reconstitute a surrogate human immune system (HIS) that can be used for studies on human immunology, which may provide a predictive preclinical model for human vaccines prior to clinical trails.

Various models of humanized mice were developed with different genetic manipulations designed to meet the needs of in vivo studies of human systems. (See Table 1). Although, the current mouse models permit long-term hematopoiesis of human B cells (2, 3). they allow poor development of functional human T cells (2-5). The current mouse models also fail to develop serum levels of human IgM and IgG comparable to that of human blood (3). This limitation has been attributed to the lack of expression of Human Leukocyte Antigens (HLA) molecules in mouse lymphoid organs. Recently, humanized mice expression HLA class I molecules have been generated but shows little improvement in human T cell reconstitution and function of T and B cells (6. 11.12). Upon vaccination, infection, or transplantation, current humanized mouse models fails to elicit immune responses in the same extent as vaccinated or infected humans (2-5. 7-9). A humanized mouse model, or a mouse-human chimera, which overcome these constraints, is described in the instant application, and in Danner R. Chaudhari SN. Rosenberger J. Expression of HLA class II molecules in humanized NOD.Rag1 KO.IL2RgcKO mice is critical for development and function of human T and B cells. PLoS One. 2011:6(5):e19826, is incorporated herein by reference in its entirety.

TABLE 1

Current Humanized Mouse Models

| Mutate allele | Phenotype | Advantage | Disadvantage |
|---|---|---|---|
| NOD-scid KO | No mature T and B cells<br>Radiation sensitive<br>Decrease innate immunity | low level of innate immunity<br>low NK-cell function<br>increased engraftment of<br>human HSCs and PBMCs | Residual innate immunity<br>Low but present NK-cell<br>activity<br>Decrease lifespan owing to<br>thymic lymphomas |
| NOD-scid KO,<br>IL2Rγ KO | No mature T and B cells<br>Radiation sensitive<br>IL-2Rγ-chain deficiently; no<br>high-affinity signaling<br>through multiple cytokine<br>receptors leading to many<br>innate-immune defects | Long lifespan<br>Further reduction in innate<br>immunity<br>NK cells absent<br>Higher level of engraftment of<br>human cells<br>Develop functional human<br>immune system<br>Complete absence of IL2rg<br>gene | Lack appropriate MHC<br>molecules for T-cell selection<br>in the mouse thymus<br>Seem to lack some human-<br>specific cytokines required for<br>human cell development and<br>survival<br>Low and variable level of T-<br>cell-dependant antibody<br>responses |
| NOD-Rag1 KO | Rag1 mutation leading to<br>lack of mature T and B cells | Radiation resistant | Residual innate immunity<br>Low but present NK-cell<br>activity<br>Low and Variable level of<br>engraftment |
| NOD-Rag1 KO,<br>IL2Rγ KO | Rag1 mutation leading to<br>lack of mature T and B cells<br>IL-2Rγ-chain deficiently; no<br>high-affinity signaling<br>through multiple cytokine<br>receptors leading to many<br>innate-immune defects | Radiation resistant<br>Long lifespan<br>Further reduction in innate<br>immunity<br>NK cells absent<br>Higher level of engraftment of<br>human cells<br>Develop functional human<br>immune system<br>Complete absence of IL2rg<br>gene | |

TABLE 1-continued

Current Humanized Mouse Models

| Mutate allele | Phenotype | Advantage | Disadvantage |
| --- | --- | --- | --- |
| NOD-scid, HLA-A2, IL2Rγ KO | Transgenic expression of human HLA-A2<br>No mature T and B cells<br>Radiation sensitive<br>IL-2Rγ-chain deficiently; no high-affinity signaling through multiple cytokine receptors leading to many innate-immune defects | Long lifespan<br>Further reduction in innate immunity<br>NK cells absent<br>Higher level of engraftment of human cells<br>Develop functional human immune system<br>Complete absence of IL2rg gene<br>Transgenic expression of human MHC molecules | Seem to lack some human-specific cytokines required for human cell development and survival<br>Low and variable level of T-cell-dependant antibody responses |
| BALB/c-Rag1 KO, | Rag1 mutation leading to lack of mature T and B cells | Radiation resistant (can survive high dose of radiation) | Residual innate immunity<br>Low but present NK-cell activity<br>Low and variable level of engraftment |
| BALB/c-Rag1 KO, IL2Rγ KO | Rag1 mutation leading to lack of mature T and B cells<br>IL-2Rγ-chain deficiently; no high-affinity signaling through multiple cytokine receptors leading to many innate-immune defects | Radiation Resistant | |

BRIEF DESCRIPTION OF THE FIGURES

FIG. 7. FIG. 5. Kinetics of human B cell reconstitution in blood of DRAG and control mice. DRAG (n=15) and control (n=11) mice were examined in peripheral blood by FACS using human CD 19 Abs. The cut-off for positive human B cells was calculated as three times the standard deviation over the background of cells from naive (non-HSC infused) DRAG mice stained with CD19 antibodies (0.18%). Panel A, percentage of human B cell reconstituted mice at various time points post-infusion of HSC. Fisher exact test indicated that the rate of human B-cell reconstitution in DRAG mice (14 out of 15) was similar to that of control mice (9 out 11) (p=0.54). Panel B, frequency of human B cells in blood of reconstituted DRAG (n=14) and control (n=9) mice (p=0.31, Mann-Whitney test). Panels C and D, plasma values of human IgM and IgG respectively in B-cell reconstituted DRAG (n=14) and control (n=9) mice at various time points post-infusion of HSC (p values 0.0002 and ,0.0001, Maim-Whitney test).

Data represent mean values of mice analyzed individually. Ranges are indicated over the plots.

DETAILED DESCRIPTION OF THE INVENTION

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The term "transgene" refers to the genetic material which has been or is about to be artificially inserted into the genome of an animal, particularly a mammal and more particularly a mammalian cell of a living animal.

"Transgenic animal" refers to a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

"Humanized mouse" refers to immunocomprimised mice engrafted with human haematopoietic stem cells or tissues, or mice that transgenically express human genes.

"Inbreeding" refers the mating of closely related individuals or of individuals having closely similar genetic constitutions.

"Backcross" refers to mating the crossbred offspring of a two-way crossback to one of the parent breeds.

One aspect of the instant invention is a transgenic animal model whose genome comprising a nucleic acid construct comprising as least one transgene linked to a promoter effective for expression of human leukocyte antigen DR4 and/or human costimulatory molecules (CD80), which develops a functional human immune system upon infusion of human HLA-matched hematopoietic stem cells.

In one embodiment, one human gene was inserted into the genome of a genetically-altered mouse already containing a human gene, thereby producing a multi-transgenic mouse.

Another aspect of the instant invention is directed to a method for producing a multi-transgenic animal in general. Typically, transgenic mice are generated by microinjecting a foreign gene into fertilized eggs isolated from a normal, nontransgenic mouse. In the instant invention, it has been shown that it is possible to create a mouse expressing additional human transgenes by starting with a mouse that is already transgenic. That is, single-cell embryos (fertilized eggs) from an existing transgenic mouse have been harvested and additional transgene DNA fragments have been microinjected into the cells. The results shown herein demonstrate that existing fertilized eggs from transgenic mice can withstand the microinjection process to successfully produce a multi-transgenic mouse.

EXAMPLE 1

Generation of DRAG and DRAG80 Mouse Strains

Two mouse strains were genetically modified to sustain the development of human hematopoietic system upon infusion of human stem cells. These strains are:

Strain #1: NOD.Rag1KO.IL2RγcKO mice expressing HLA-DR4, thereafter referred as DRAG mice. Strain #2: HLA-DR4 Tg, hCD80 Tg, Rag1KO, IL2RγKO (NOD background), thereafter referred as DRAG80 mice.

Other mouse strains obtained during from process for generation of above strains are: Strain #3: HLA-DR4 Tg, Abb KO, Rag2 KO (C57BL/6 background). Strain #4: HLA-DR4 Tg, hCD80 Tg, Abb KO, Rag2 KO (C57BL/6 background)

TABLE 2

Outcome and Purpose of the Genetic Modification of Mice Strain Used

| Genotype: | Outcome: | Purpose: |
|---|---|---|
| 1. Rag2 KO | Lack of mouse T and B cells | to prevent rejection of human cells |
| 2. HLA-DR4 Tg | Expression of human MHC II on thymic stroma and peripheral APCs | to favor positive selection of human T cell precursors in thymus and antigen-presentation in periphery |
| 3. hCD80 Tg | Expression of human costimulatory molecule CD80 (B7.1) | to sustain activation/survival signals in mature T cells in periphery |
| 4. Abb KO | Lack of endogenous mouse MHC II molecules | to prevent GvH by human T cells |
| 5. NOD background | Permissive strain | favor HSC engraftment |
| 6. IL2Rγ KO | Lack of mouse NK activity | enhance HSC engraftment |

Abbreviations: HLA-DR4: Human Leukocyte Antigen DR*0401; Rag2: recombination activation gene 2; Tg: transgenic; KO: knockout; Abb: mouse MHC class II (I-Ab)

The DRAG and DRAG80 mouse strains were created following sequential steps that are illustrated in FIGS. 1-4.

Step 1. Generation of HLA-DR4 Tg, Abb KO, Rue KO mice in C57BL/6 Background

Figure 1:
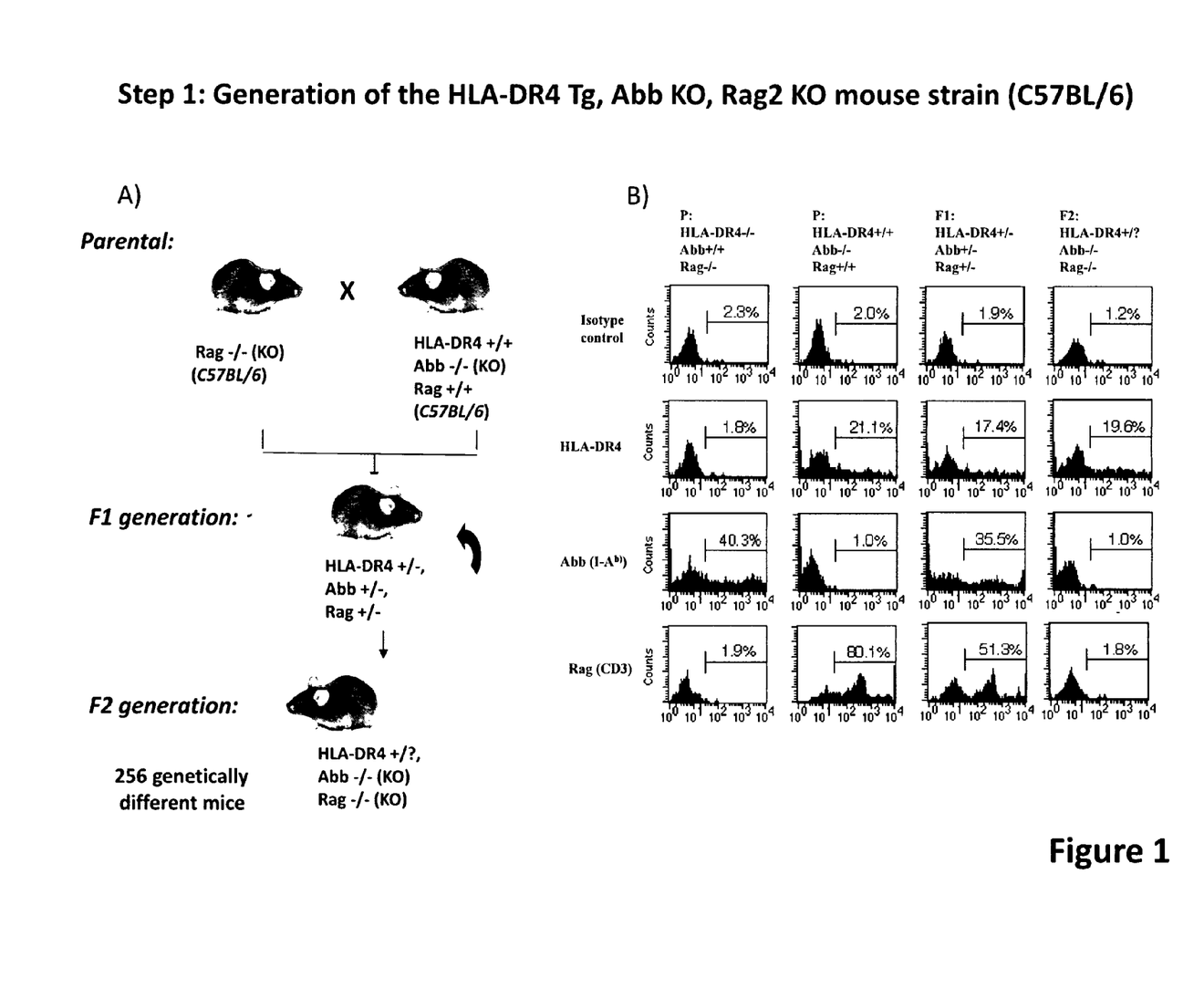
FIG. 1. Generation of HLA-DR4 Tg, Abb KO, Rag2 KO mice (C57BL/6 background): Panel A, breeding strategy, Panel B, characterization of mice by FACS.

C57BL/6 mice expressing transgenically HLA-DR4 (HLA DR*0401/I-$E^d$) molecules under mouse I-$E^d$ promoter (line 4149) (Taconic Farms, Inc., New York), and Rag2 KO C57BL/6 mice (Taconic Farms, Inc., New York) are used as parental (P) mice to generate F1 mice that are heterozygous for all target genes of the parent mouse (HLA-DR4, Abb KO, and Rag2) (FIG. 1). F1 mice are then intercrossed to generate F2 mice that were screened for expression of HLA-DR4 Tg and KO mutations for Rag2 and Abb loci. Screening of mice was performed by FACS analysis using specific antibodies and confirmed by PCR. As shown in FIG. 1, panel B, F2 mice that expressing HLA-DR4 molecules, and KO for Abb and Rag2 genes were selected. This novel mouse strain F2 (HLA-DR4 Tg, Abb KO, Rag2KO in C57BL/6 background) is currently maintained at the WRAIR VetMed facility.

Step 2. Generation of HLA-DR4 Tg, hCD80 Tg, Abb KO, Rag2 KO Mice in C57BL/6 Background (M3)

Figure 2:
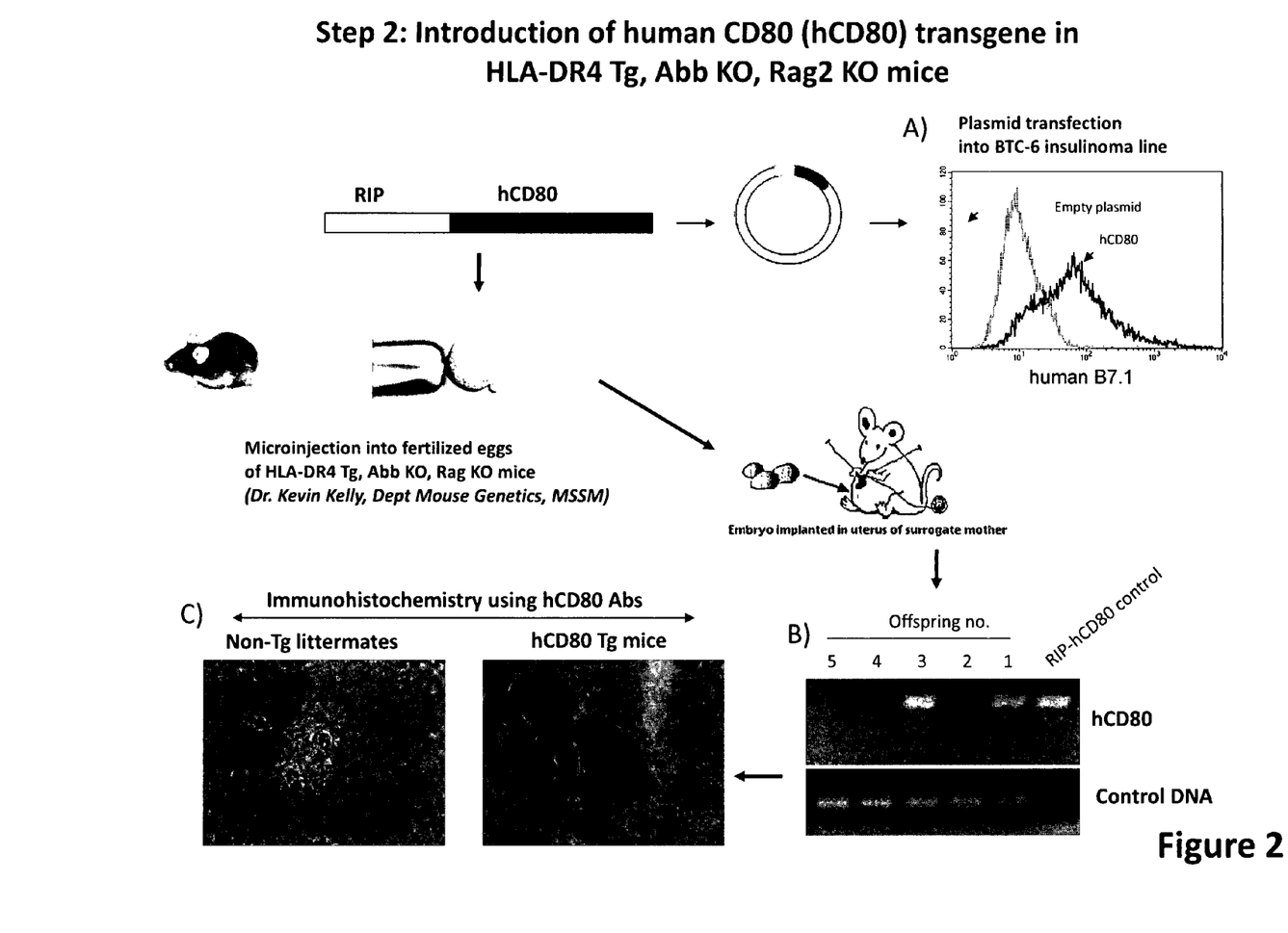
FIG. 2. Introduction of human CD80 (hCD80) transgene in HLA-DR4 Tg, Abb KO, Rag2 KO mice. Panel A shows expression of hCD80 by transfected BTC-6 insulinoma cells. Panel B shows PCR screening of littermates obtained by microinjection of RIP-hCD80 construct. Panel C, expression of hCD80 in pancreatic beta cells from hCD80 Tg littermates (right panel). No staining was detected in pancreatic beta-cells from non transgenic littermates (left panel).

The C57BL/6 mouse expressing transgenically HLA-DR4 and hCD80 molecules, and showing knock out mutation of the Abb, Rag2 loci (M3) is generated by microinjection of RIP-hCD8 DNA into fertilized eggs of F2 mice (HLA-DR4 Tg, Abb KO, Rag2 KO in C57BL/6 background) (FIG. 2).

Genetic Construction of RIP-hCD80: The gene encoding for human CD80 (hCD80) was cloned by RT-PCR from total RNA extracted from Boleth (human B lymphoblastoma) cells. The genomic region of rat insulin promoter (RIP) was cloned by PCR from DNA extracted of splenic cells of RIP-HA Tg mice (a gift from Dr. Harald von Boehmer at INSERM, France) (11). Primers used for cloning of hCD80 gene and RIP contained restriction sequences that allowed the assembling of RIP and hCD80 in frame. To assess the structural integrity and the ability of the chimeric RIP-hCD80 genetic construct to express hCD80 protein, the RIP-hCD80 genetic construct was cloned in a pcDNA3 vector, and used to transfect BTC-6 mouse insulinoma cells. FIG. 2A demonstrated hCD80 expression on transfected cells.

Generation of HLA-DR4 Tg, hCD80 Tg, Abb KO, Rag2 KO Mice: The RIP-hCD80 construct was introduced into fertilized eggs of HLA-DR4 Tg, Abb KO, Rag2 KO mice (F2). The developed embryos were implanted in uterus of surrogate female dams, using standard procedures at the Mouse Genetics Core, Mount Sinai School of Medicine, New York, N.Y. Progeny was screened by PCR using specific primers for the RIP-CD80 genetic construct (FIG. 2B). Expression of hCD80 in pancreatic beta-cells from Transgenic littermates was assessed by immunohistochemistry using anti-hCD80 Abs. The results were shown in FIG. 2C, right panel demonstrated expression of hCD80 Tg in pancreatic beta-cells. This new mouse strain M3 (HLA-DR4 Tg, hCD80 Tg, Abb KO, Rag2 KO) is currently maintained at WRAIR VetMed facility.

Step 3. Generation of DRAG Mice (HLA-DR4 Tg, Rag1KO, IL2γ KO in NOD Background) And DRAG80 Mice (HLA-DR4 Tg, hCD80, Rag1KO, IL2RγKO in NOD Background)

Figure 3:
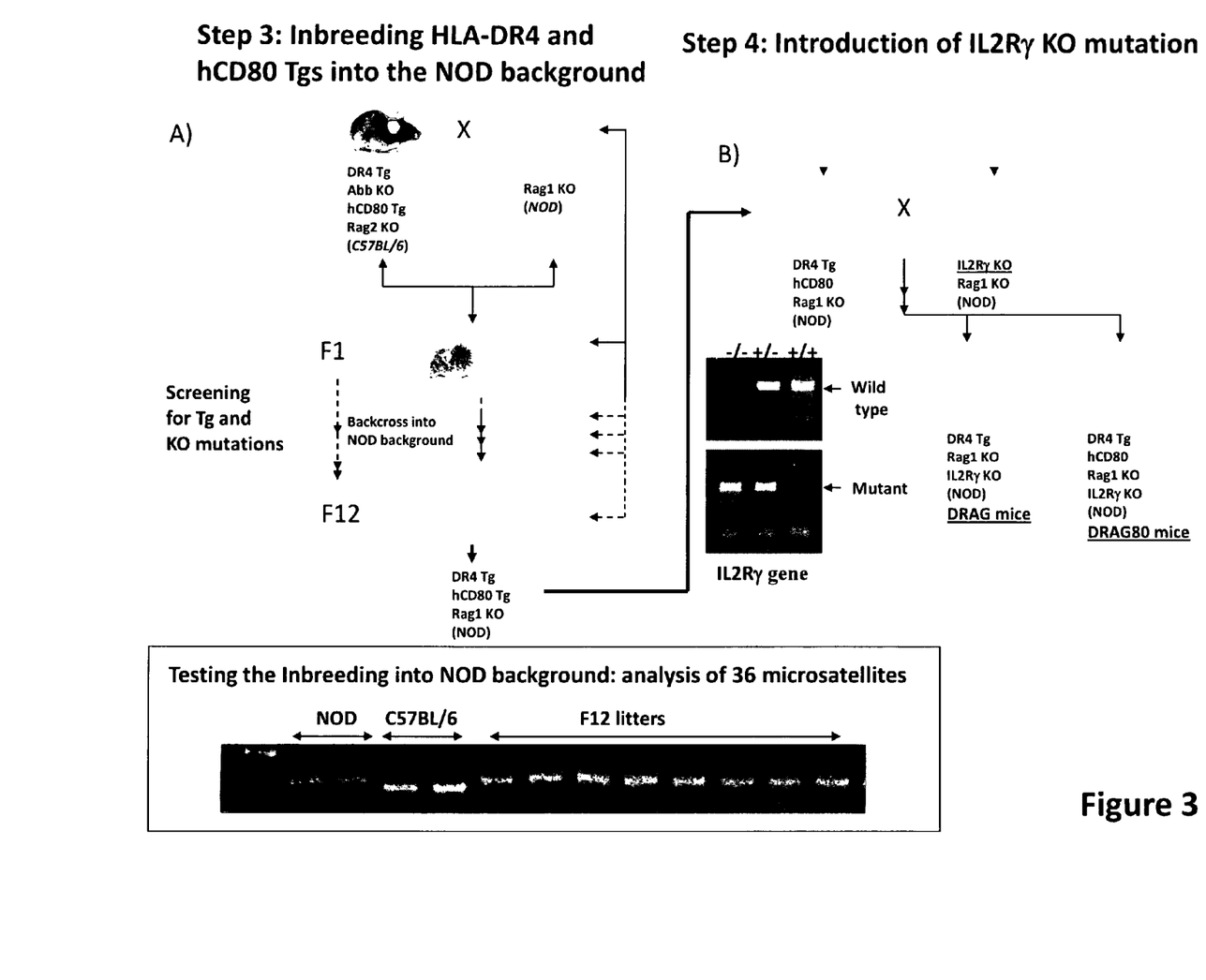
FIG. 3. Generation of HLA-DR4 Tg, Rag1KO, IL-2R γ KO (DRAG) and HLA-DR4 Tg, hCD80, Rag1KO, IL-2Rγ KO (DRAG80) mice.

The DRAG and DRAG80 mouse strain were generated by inbreeding the HLA-DR4 and hCD80 Tg from the F2/M3 mouse strain into the NOD/Rag1 background (FIG. 3A), followed by introduction of the IL2Rγ KO mutation into their genetic background (FIG. 3B)

FIG. 3A is a schematic representation showing the inbreeding the hCD80 Tg into the NOD background. C57BL/6 mice expressing transgenically HLA-DR4 molecules (F2) or C57BL/6 mice expressing transgenically HLA-DR4 and hCD80 molecules, and with knock out mutation at Abb, and Rag2 loci were backcrossed with Rag1KO mice in NOD background (The Jackson Laboratories, Bar Harbor, Me.) for twelve generations. Litters from each generation (F1-F12) were screened for mice were screened for HLA-DR4 using specific primer sets (SEQ ID NOs. 1-4) or hCD80 Tgs, and Rag1 KO mutations. Rag1 KO litters were identified by the absence of CD3$^+$ T cells upon staining of peripheral blood cells with anti-mouse CD3 (BECKTON DICKINSON™, San Jose)

The level of inbreeding of F12 mice in the NOD background was 100%, as determined by microsatellite analysis (Mappairs, Diversified Biopharma Solutions Inc., Loma Linda, Calif.) (FIG. 3A, lower panel). F12 mice showed complete microsatellite identity with NOD for the 36 microsatellite regions.

Next, F12: HLA-DR4 Tg, hCD80 Tg, Rag1 KO (NOD) and F12:HLA-DR4 Tg, Rag1 KO (NOD) male mice were crossed with IL2RγKO, Rag1KO (NOD) female mice (The Jackson Laboratories, Bar Harbor, Me.) (FIG. 3B) and the male progeny was screened for HLA-DR4 transgene (the IL2Rγ gene is located in the X chromosome). Positive males were crossed with NOD.Rag1 KO. IL2RγKO females and all progeny were screened via PCR for HLA-DR4 and hCD80 Tgs and IL2RγKO mutations (FIG. 3B). Mice having the genotype HLA-DR4 Tg, Rag1KO, IL2Rγ KO (strain #1, DRAG), and mice having the genotype HLA-DR4 Tg, hCD80 Tg, Rag1KO, IL2RγKO (strain #2, DRAG80) were selected. These new mouse strains are currently maintained at the WRAIR VetMed Facility.

EXAMPLE 2

Functionality Testing of Transgenic Mouse

Figure 8:
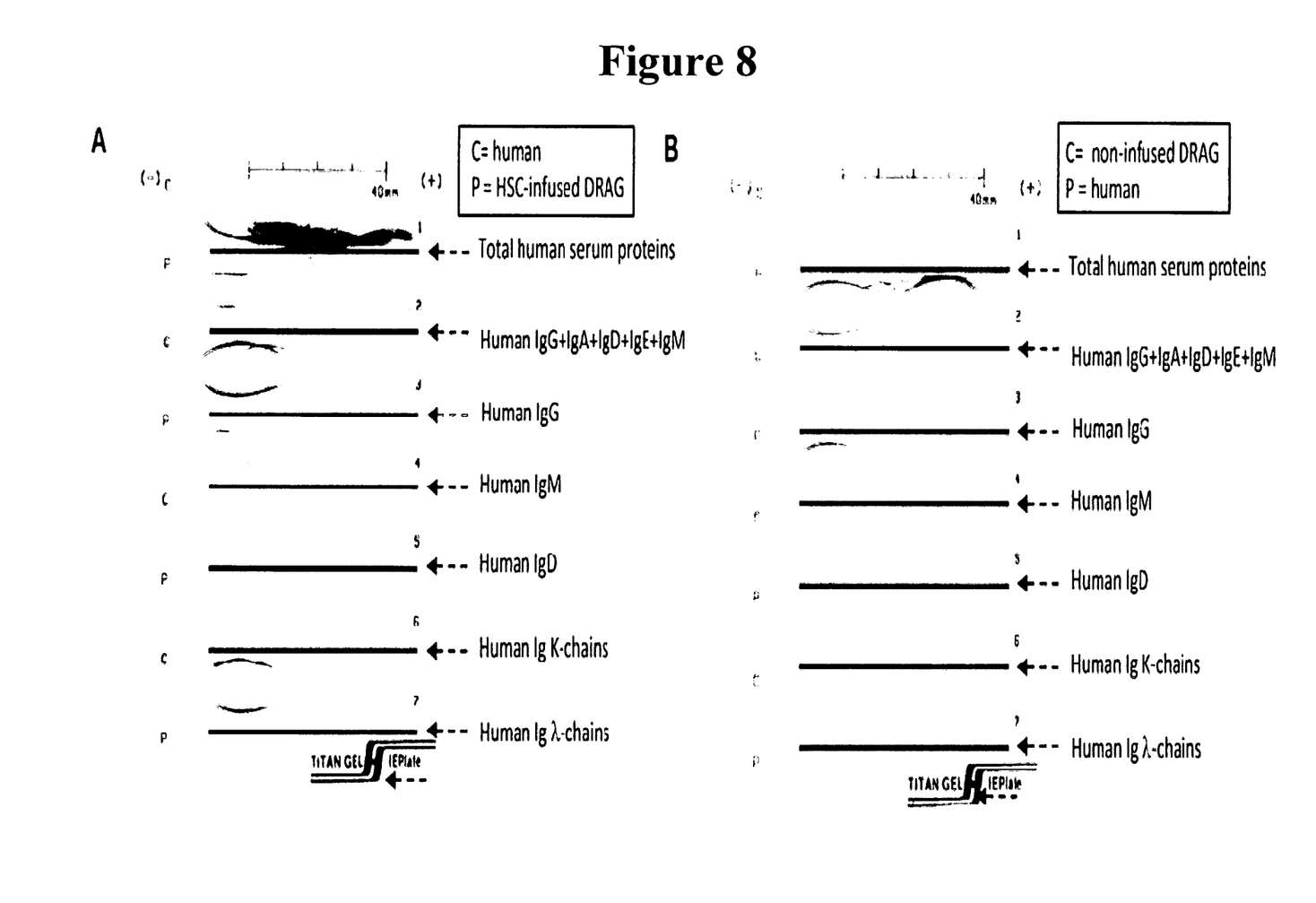
FIG. 8. B cells from DRAG mice undergo immunoglobulin class switching. Panels A and B, immunoelectrophoresis of plasma proteins from DRAG mice at 6 months post-infusion of HSC or prior to infusion with HSC, respectively. Panel C, percentage of human IgG subclasses within the total human IgG fraction in plasma of six DRAG mice examined. Panel D, 12 out 14 (85.7%) DRAG mice that showed human B cells in blood, reconstituted human IgA in plasma. Data present mean values of mice analyzed individually. Panel E, 7 out of 14 (50%) DRAG mice also reconstituted human IgE in plasma. No human IgA or IgE was detected in plasma of control mice (p values, 0.0001 and 0.015, respectively by Mann-Whitney test).
Figure 9:
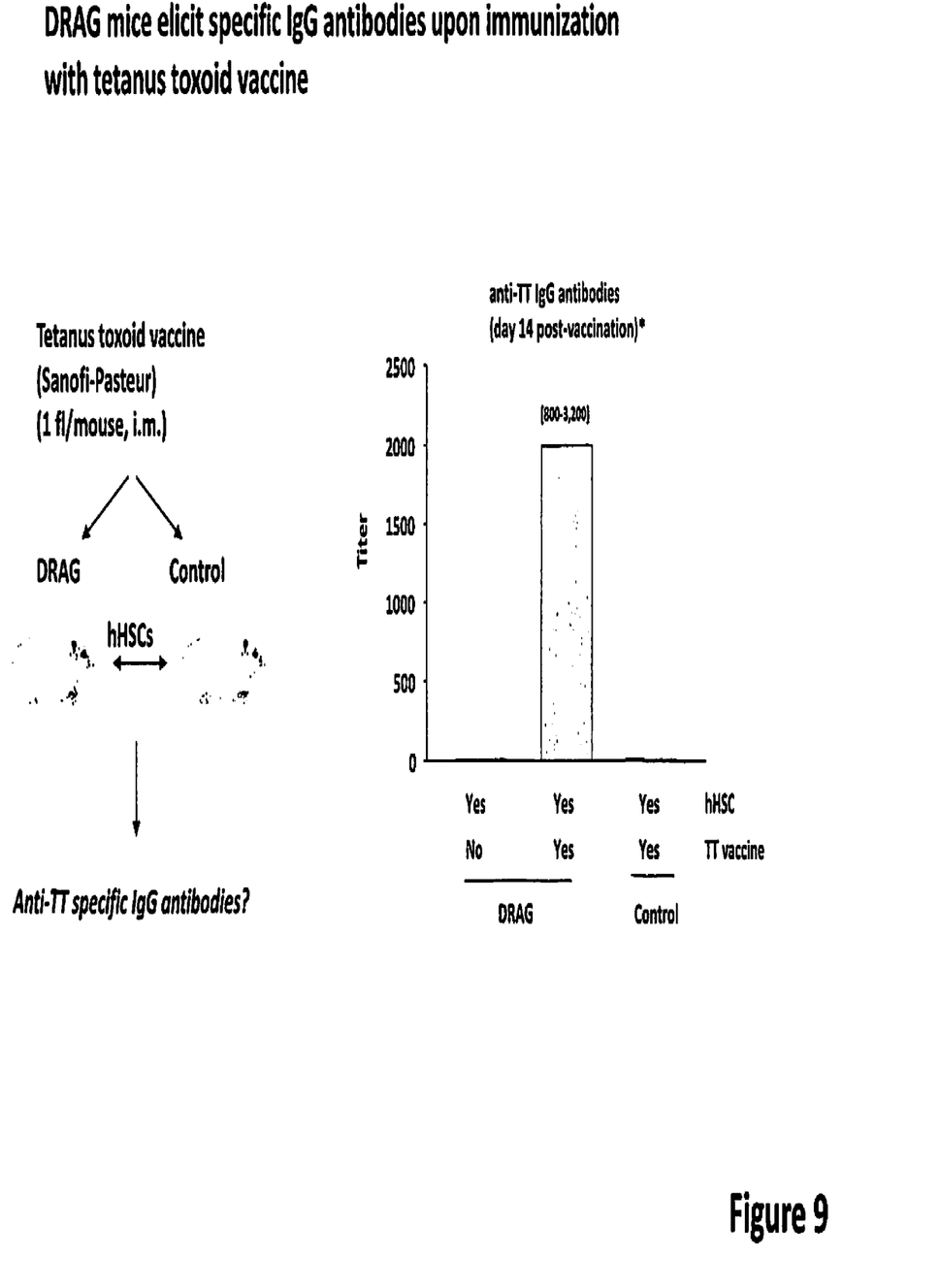
FIG. 9. DRAG mice respond to TT vaccination. DRAG and control mice were immunized with TT vaccine and serum levels of anti-TT IgG were measured at day 14 post-immunization by ELISA. Data show that DRAG mice elicited anti-TT IgG antibodies whereas control mice failed to do so.

The newly-developed humanized mice DRAG (HLA-DR4 Tg, Rag1 KO, IL2RγKO and DRAG80 (HLA-DR4 Tg, hCD80, Rag1KO, IL2R KO DRAG80) are superior than the current humanized mouse strains (NOD-scid KO; NOD-scid KO, IL2Rγ KO; NOD-Rag1 KO, NOD-Rag1 KO IL2Rγ KO; BALB/c-Rag1KO; and BALB/c-Rag1 KO, IL2R IL2Rγ KO). They are capable of:

1) providing high level of human T cell reconstitution and frequencies of CD4 T and CD8 T cell subsets (FIG. 4)
2) allowing development of human regulatory CD4+ FOXP3+ T cells (FIG. 6)
3) allowing development of serum levels of human IgM and IgG comparable to human blood (FIG. 6C, FIG. 7)
4) allowing development of human IgG1, IgG2, IgG3, IgG4 subclasses (FIG. 8) and
5) providing the ability to elicit specific IgG antibodies upon vaccination (FIG. 9)

To test the functionality of the new strain of transgenic mouse, mice were infused with human hematopoietic stem cells (HSC). Umbilical cord blood (UCB) were purchased from AllCells (Emeryville, Calif.) and Promocell (Heidlbery, Germany). Screening were carried out using DRB1*04 SSP Unitray (INVITROGEN®, San Diego, Calif.). HLA-DRB1*04-positive cord bloods were enriched for CD 34+ stem cells using Easy Sep, Human Progenitor Cell Enrichment kit (StemCell Technologies, Vancouver, BC). Prior to enrichment, the frequency of CD 34+ cells in UCBs were 1.0±5% and after enrichment 62.0±8.6%. 4-6 week old mice were irradiated at (350-450 rads), and injected intravenously with 40,000-80,000 human hematopoietic stem cells.

The mice tested were DRAG mice (HLA-DR4 Tg, Rag1KO, IL2Rγ KO in NOD background). As control, Rag1KO, IL2Rg KO littermates (negative for HLA-DR4 and hCD80 Tgs) were used. The control mice are identical to the commercial strain NOD-Rag1 KO, IL2Rγ KO. Their use allowed a strict comparison between the control and the test mouse models. Previous studies demonstrated no significant difference between NOD-Rag1 KO, IL2R littermates and the other commercial strains in terms of development of a human immune system (3, 4).

Results

Higher Level of Human T Cell Reconstitution and Frequencies of CD4 T and CD8 T Cell Subsets In DRAG Mice as Compared to Control Mice.

Pre-T cells derived from differentiation of hematopoietic stem cells in the bone marrow migrate to the thymus to undergo either positive (survival) or negative (deletion) selection upon recognition of self-peptides presented by thymic stromal cells in the context of MHC molecules. This is a physiological process aimed at preventing autoimmunity, by means of elimination of T cells that can react against self-antigens. T cell precursors in thymus that are positively selected receive survival signals that enable them to migrate and repopulate peripheral lymphoid organs (12).

Current humanized mouse models do not express human MHC (HLA) molecules and consequently the differentiation of T cells is thought to occur extra-thymically. Extra-thymic differentiation of human T cells in the current humanized mouse models may thus account for poor human T cell development and function, as it has been widely reported (2-9). Transgenic mouse described in the application (DRAG mice) express transgenically HLA-DR4 molecules and consequently they are expected to allow thymic differentiation of T cell precursors derived from HLA-matched hHSCs.

To test this hypothesis, groups of DRAG mice and control mice were injected with human HSC of HLA-DR4 haplotype, and they were followed for development of human T cells in peripheral blood by FACS. Blood drawn for the tail vein was collected with heparin-coated capillary tube. Erythrocytes were lysed using ACK lysis buffer and white blook cells were incubated with Fcblock and strined with anti-human CD3, CD4, CD8 and CD19 Abs (BD® biosciences) and washed with PBS/1% BSA/0.1% Na azide and analyzed by BACS on mononuclear FSC/SSC scatter. Human peripheral blood from adult healthy volunteers was used as controls and was collected and treated as above. The analyses were performed at various time points upon human HSC infusion.

Development of Functional Human T Cells

To assess the function of human T cells developed by DRAG, groups of mice (both DRAG and control) were euthanized and splenic T cells adjusted to 3×105 from mice or PBMCs (3×10$^5$) were stimulated with anti-human CD3/CD28-coated magnetic beads. Stimulation with CD3/CD28 antibodies is a common approach to test selectively the function of T cells. Cytokines in supernatants were measured by Luminex (INVITROGEN® CA).

Spleen cells adjusted to 3×10$^6$ cells/ml were depleted of CD4 T cells, CD8 T cells, or both cell subsets with antibody-coated magnetic beads (Dynabeads, InVitrogen). The efficiency of cell depletion was 0.95% as measured by FACS using CD3, CD4, and CD8 Abs. Equal volumes (0.1 ml) of cell depleted cell suspensions or corresponding volumes of positively isolated cells on the magnetic beads were stimulated with PMA/iomycin for 24 h and cytokine secretion in cell culture supernatants were measured by (INVITROGEN® CA).

Figure 4:
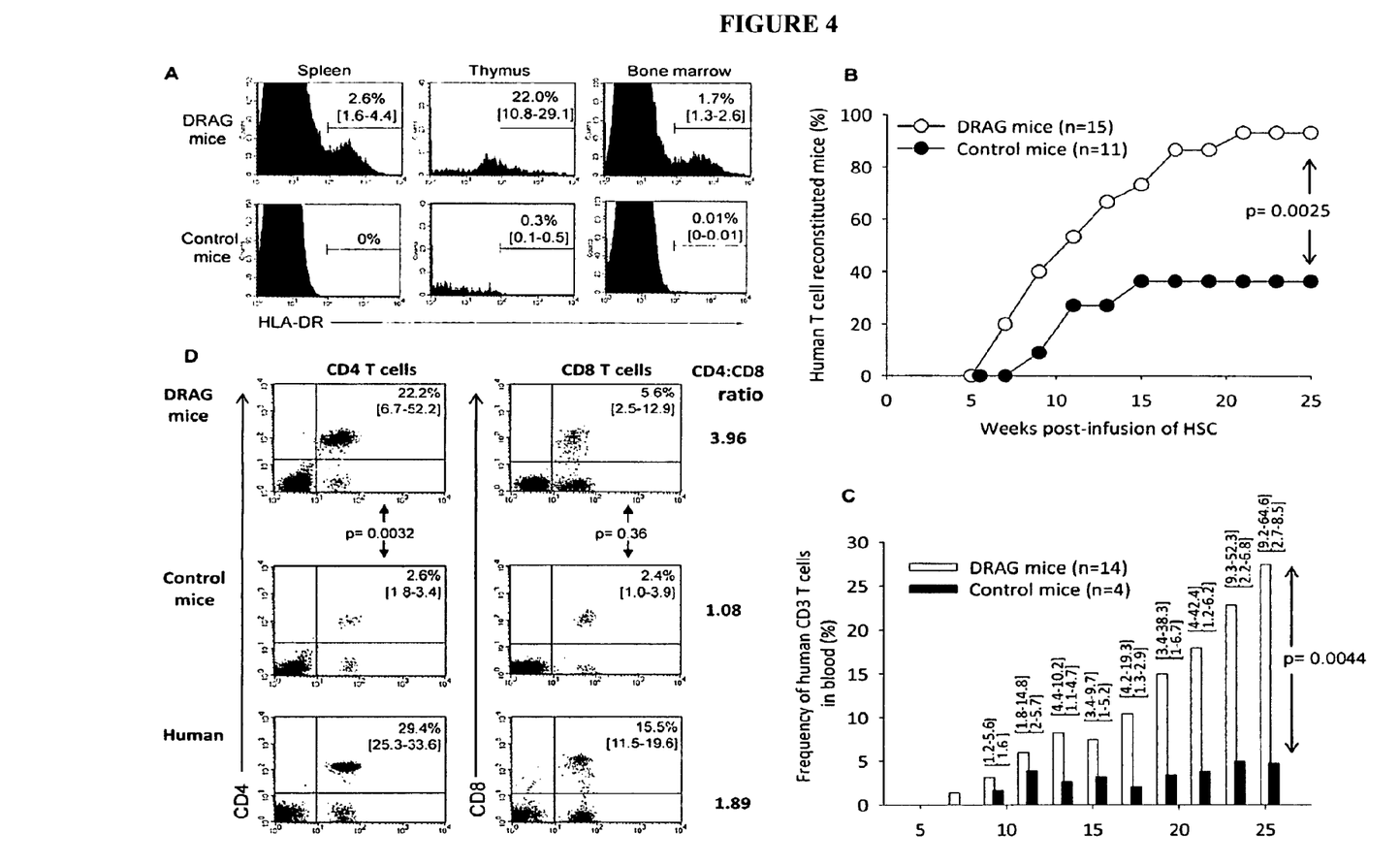
FIG. 4. Kinetics of human T cells reconstitution in blood of DRAG mice.

As illustrated in FIG. 4, Panel A, FACS analysis of splenic, thymic, and bone marrow cells from naive (non-HSC infused) DRAG and control mice (n=3) stained with HLA-DR antibodies. Groups of DRAG (n=15) and control (n=11) mice that were infused intravenously with 80,000 enriched-HSC (CD34+) cells from umbilical cord blood of HLA-DR4 (*0401) newborns were examined in peripheral blood by FACS using anti-human CD3, CD4, and CD8. Panel B shows percentage of human T cell reconstituted mice at various time points post-infusion of HSC. Fisher exact test indicated that the rate of human T-cell reconstitution in DRAG mice (14 out of 15) was significantly superior to that in control mice (4 out of 11) (p=0.0025). In addition, Mann-Whitney test indicated that the frequency of human T cells in blood of DRAG mice was significantly higher than that in control mice (p=0.0044). The cut-off for positive human CD3+ T cells was calculated as three times the standard deviation over the background levels of cells from naive (non-HSC infused) DRAG mice that were stained with anti-human CD3 (0.17%). Ranges are indicated over the plots. Thus, the results demonstrated that expression of HLA-CD4 molecules in DRAG mice promoted development of human T cells. Panel D shows frequency of human CD4 and CD8 T cells in blood of T cell reconstituted DRAG mice (n=14) and control mice (n=4) at 25 weeks post-infusion of HSC (upper two panels). Lower histograms shows frequencies of CD4 and CD8 T cells in human blood (n=2). P values were calculated using the Mann-Whitney test. T cell-reconstituted DRAG (n=14) and control mice (n=4) developed both CD4 and CD8 T cells in blood, but the frequency of CD4 T cells was significantly higher in DRAG mice (FIG. 4D, p=0.0032). Of note, the frequency of blood circulating CD4 T cells in DRAG mice was comparable to that of human volunteers (FIG. 4D, upper and lower panels). On the other hand, the frequency of human CD8 T cells in blood of both groups of mice was similar (FIG. 4D, p=0.36) and at the same time lower than that in blood of human volunteers. T cell-reconstituted DRAG (n=14) and control mice (n=4) developed both CD4 and CD8 T cells in blood, but the frequency of CD4 T cells was significantly higher in DRAG mice (FIG. 4D, p=0.0032). Of note, the frequency of blood circulating CD4 T cells in DRAG mice was comparable to that of human volunteers (FIG. 4D, upper and lower panels). On the other hand, the frequency of human CD8 T cells in blood of both groups of mice was similar (FIG. 4D, p=0.36) and at the same time lower than that in blood of human volunteers.

Figure 5:
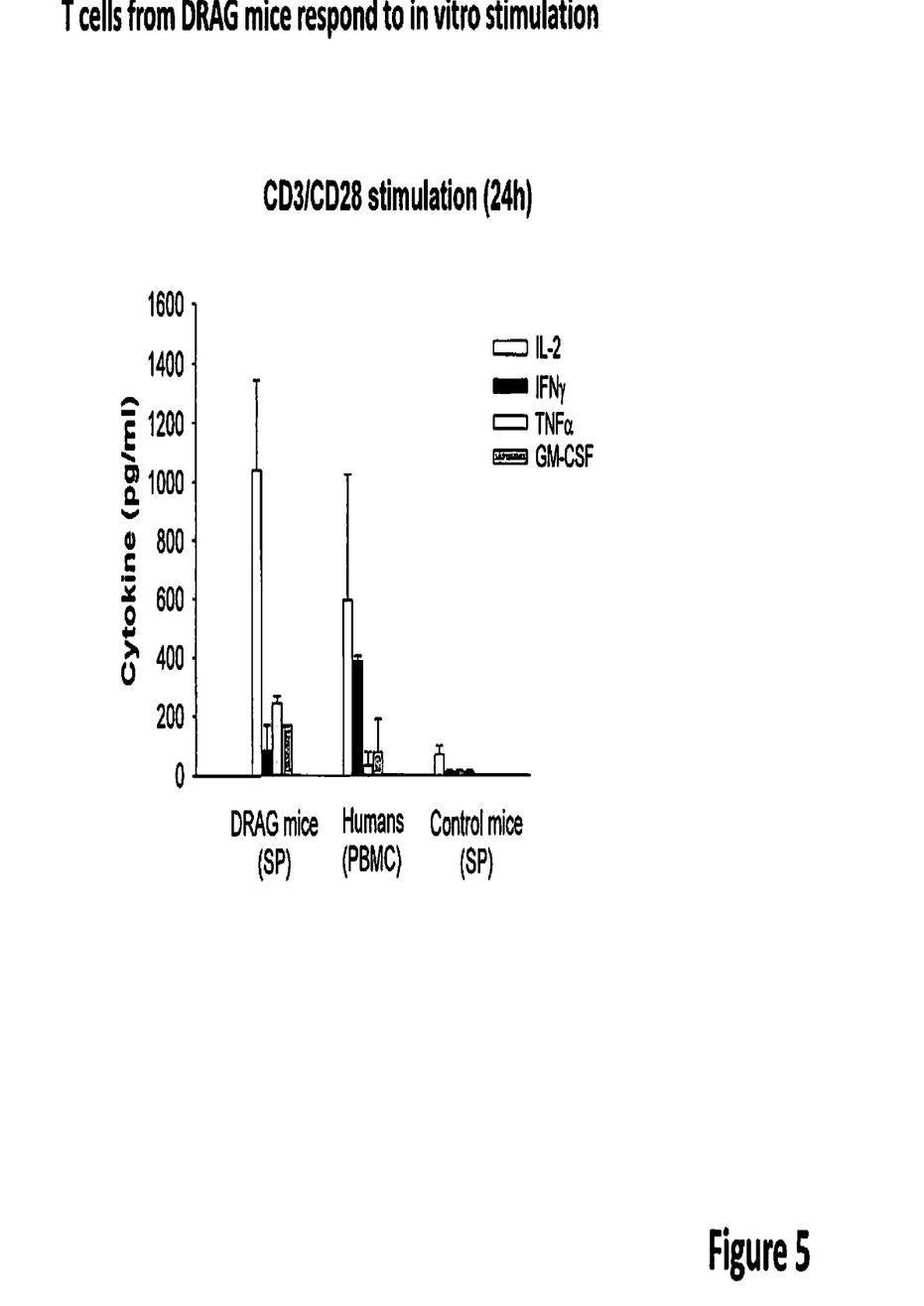
FIG. 5. T cell response in DRAG mice. Splenic cells ($3 \times 10^5$) from DRAG or control mice were stimulated in vitro with anti-human CD3/CD28 Abs. As control, human PBMC ($3 \times 10^5$) were also stimulated with CD3/CD28 Abs.

As illustrated in FIG. 5, the T cells from DRAG mice, but not T cells from control mice, responded vigorously to CD3/CD28 stimulation, as measured by the level of cytokines secreted in cell culture supernatants. The lack of T cell response in control mice is in agreement with previous studies indicating that T cells from stem cell-reconstituted NOD-scid respond poorly to CD3/CD28 stimulation in vitro (3). On the other hand, T cell response of DRAG mice was similar to that of T cells from human blood. This result demonstrated that T cells from DRAG mice are fully functional, whereas the T cells from control mice are impaired in function.

Development of Human Regulatory CD4+ FOXP3+ T Cells

Figure 6:
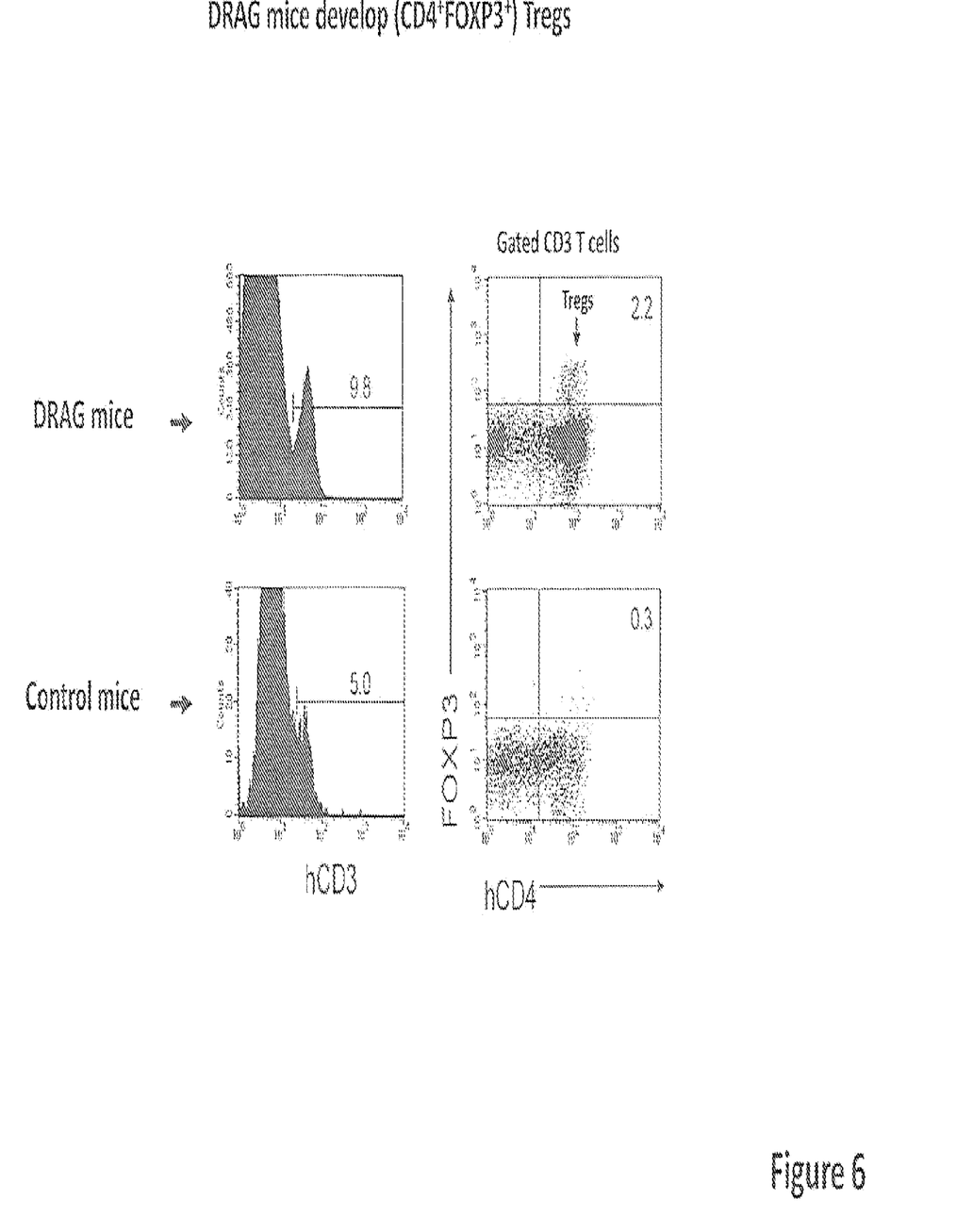
FIG. 6. Development of regulatory CD4+ FOXP3+ T cells (Tregs) by DRAG mice. Splenic cells from DRAG and control mice were stained with anti-human CD3, CD4, FOXP3 Abs and analyzed by FACS. Data shows frequency of Tregs in DRAG mice.

Regulatory T cells, particularly those from the CD4$^+$ FOXP3$^+$ subset (Tregs), are an important compartment of the immune system, whose function is to maintain self-tolerance in periphery and to down-regulate aggressive immune responses to pathogens once the infection has been cleared. Development of Tregs by the current humanized mouse model has not been reported in the literature. However, as illustrated in FIG. 6, at 6 months after infusion of HSC, a much higher frequency (p=0.021) of human CD4$^+$ FOXP3$^+$ Tregs was detected in spleens of DRAG mice as compared to control mice. Thus, our results indicated that a major regulatory cell compartment (CD4$^+$ FOXP3$^+$ Tregs) was also reconstituted in DRAG mice upon infusion of HLA-DR-matched HSC.

Dendritic cells (DCs) are critical components of the innate immune system due to their potent ability to process antigen and present immunogenic peptides to T cells for activation. The frequency of DCs in human spleen has been estimated as 2.3% of the mononuclear population [As illustrated in table 2, both DRAG and control mice developed human DCs (CD 11c$^+$ CD 19–). The frequency of human DCs in spleens of DRAG mice (2.9%) was slightly higher than that in control mice (1.5%), though it did not reach statistical significance.

Natural killer (NK) cells are characterized by expression of CD 16, an immunoglobulin Fc receptor that allows them to eliminate target cells through a process known as "antibodydependent-cell-cytotoxicity" or ADCC. The frequency of NK cells in human spleen has been estimated as 15%. As shown in table 2, the numbers of human NK cells in both DRAG and control mice were insignificant (0.05% vs. 0.07%), which indicated that expression of HLA-DR4 did not improve development of human NK cells. In aggregate, these results demonstrated that expression of HLA-DR4 molecules in DRAG mice favored engraftment of HSC in bone marrow, homing and development of bone-marrow derived human T cell precursors in thymus, and proficient repopulation of peripheral lymphoid organs with mature CD4 and CD8 T cells. Expression of HLA-DR4 molecules however did not improve development of human NK cells.

TABLE 2

|  | DCs (CD11c$^+$CD19$^-$) | NK cells (CD16$^+$CD3$^-$) |
| --- | --- | --- |
| DRAG mice | 2.9% [1.3-444] | 0.05% [0.02-0.08] |
| Control Mice | 1.5% [0.7-2.4] P = 0.345 | 0.07% [0.05-0.08] P = 0.459 |

DRAG Mice Infused with HLA-DR-Matched HSC are Highly Reconstituted with Human B Cells The longitudinal FACS analysis in blood of DRAG and control mice using anti-human CD 19 revealed that the rate of human B-cell reconstitution was similar between the two strains.

Figure 7:
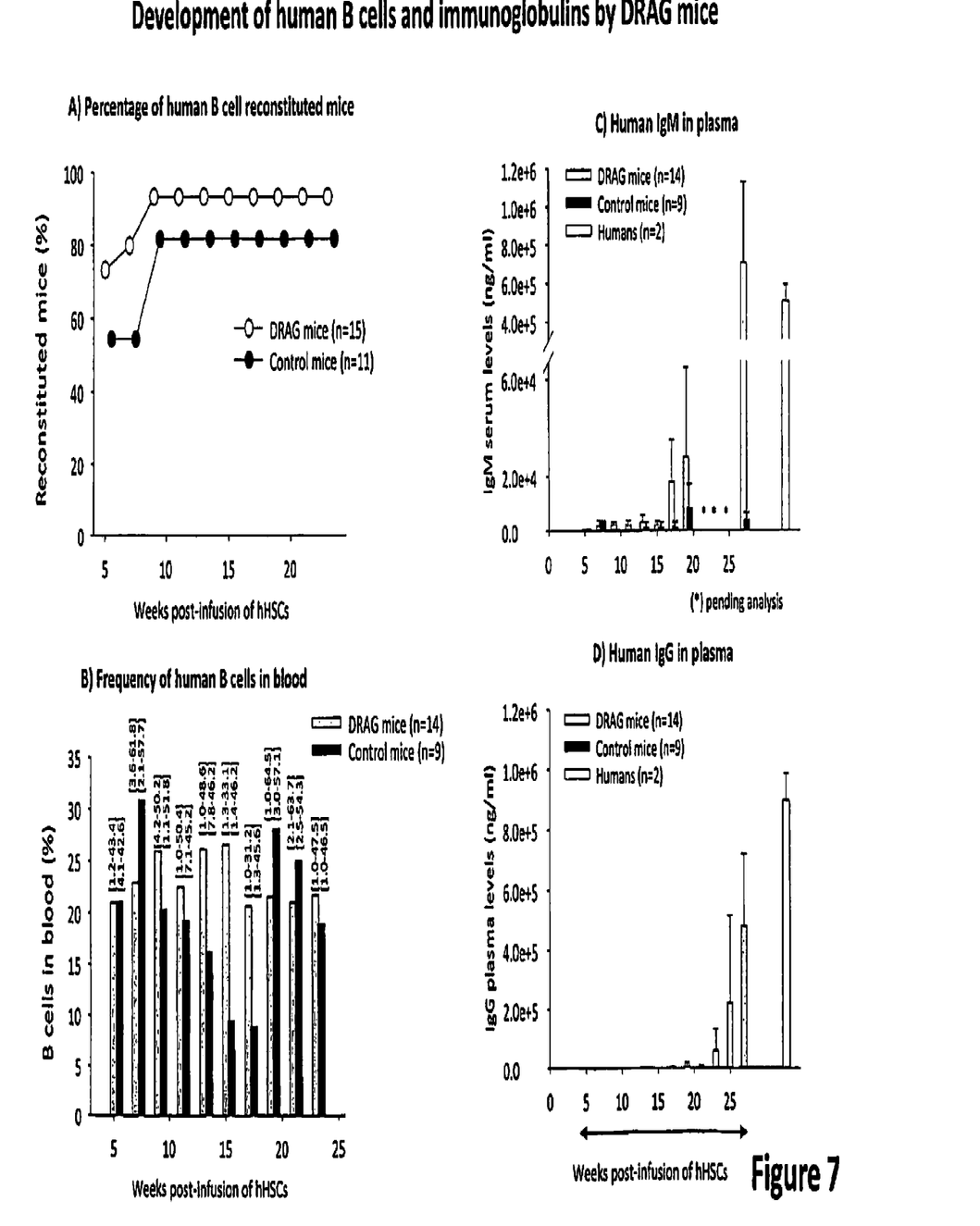

Thus, 14 out of 15 (93.3%) DRAG mice and 9 out of 11 (81.8%) control mice were reconstituted with human B (CD $19^+$) cells by 10 weeks after HSC infusion (FIG. 7A). Although not statistically significant (p=0.31), 25 weeks after infusion of HSC the overall frequency of blood circulating human B cells in DRAG mice was slightly lower than in control mice (FIG. 7B). Noteworthy, spleens of DRAG mice contained similar numbers of human B cells as compared to control mice (B cell frequency: 47.9%, range [45.9-50] vs. 60% [55-65.9]; total number of B cells/spleen: 5.5610661.95 vs. 6.35610662.75, respectively). This indicated that expression of HLA-DR4 molecules in DRAG mice did not improve significantly the reconstitution with human B cells in the peripheral blood on in the spleen as compared to control mice.

The function of B cells is to secrete antibodies (immunoglobulins) that are mainly found in blood and body fluids. The function of immunoglobulins is to counterattack pathogens such as viruses, bacteria, and parasites as well as to control the homeostatic growth of commensal bacteria in the intestinal tract (reviewed in 14). In mammalians there are five classes of immunoglobulins, namely IgD, IgM, IgG, IgA, and IgE.

In physiological conditions, IgD is found only on the surface of B cells. Upon antigen encountering, B cells undergo a rearrangement at the DNA level to switch antibody class from IgD to a secretory form of IgM. Fully functional B cells then undergo a further DNA rearrangement to switch class from IgM to either IgG, IgA, or IgE. The IgG class is by far the most abundant immunoglobulin in blood.

Thus, we investigated the kinetics of human immunoglobulin reconstitution in blood of DRAG mice. As illustrated in FIG. 7C, the levels of human IgM in plasma from B cell reconstituted DRAG mice (n=14) were significantly higher than those from reconstituted control mice (n=9) (p=0.0002). In addition, the DRAG mice were able to reconstitute plasma IgG whilst control mice failed to do so (FIG. 7D). The results indicated that the mechanism of immunoglobulin class switch was preserved in DRAG mouse. The human identity of Ig heavy chain and light chains in blood of DRAG mice was confirmed by immunoelectrophoresis (FIG. 8 A). Human IgG class comprises four different subclasses that differ in structure and biological functions, namely (i) ability to cross placenta, (ii) ability to activate the complement cascade and (iii) affinity binding to Fc receptors expressed on phagocytic cells. As illustrated in FIG. 8C, DRAG mice reconstituted plasma levels of all human IgG subclasses, with IgG2 as the most prevalent followed by IgG1, IgG3 and IgG4, whereas in the human blood the most prevalent subclass is IgG1, followed by IgG2, IgG3 and IgG4. In addition, 12 out of 14 (85.7%) DRAG mice reconstituted plasma levels of human IgA (FIG. 8D) and 7 out of 14 (50%) reconstituted plasma levels of human IgE (FIG. 8E). In contrast, control mice did not show detectable levels of human IgA or IgE (FIGS. 8D&E). The results demonstrated that human B cells developed by DRAG were functional as they secreted all human immunoglobulin classes, whereas those from control mice were impaired in their ability to undergo class switching and secreted only IgM.

Ability to Elicit Specific IgG Antibodies Upon Vaccination

A major function of the immune system is to protect against infections by eliciting specific antibodies that bind to and eliminate pathogens. Tetanus toxoid, a formalin-detoxified form of *Clostridium tetani* toxin adjuvanted in alumn, is a licensed human vaccine that induces neutralizing anti-tetanus toxin (TT) IgG antibodies. We investigated whether human B cells from DRAG mice could elicit specific humoral responses upon immunization with TT vaccine. Groups of HSC-infused DRAG and control mice were immunized with 1 flocculation unit of TT vaccine (Sanofi Pasteur) by the intramuscular route, and the titers of anti-TT IgG Abs were measured by ELISA 14 days later. As illustrated in FIG. 9, immunized-DRAG mice were able to elicit anti-TT IgG antibodies, whereas the control mice failed to do so. These results clearly indicated that human B cells developed by DRAG mice are fully functional. In addition, the results demonstrated that the "human immune system" developed by DRAG mice is superior to that developed by BLT mice, currently referred as the golden standard for humanized mice, since the BLT mice cannot elicit specific IgG antibodies upon TT immunization.

PROPHETIC EXAMPLE 3

Functionality Test for DRAG80

Experiments similar to those contained in Example 2 are conducted to test the functionality of DRAG80.

REFERENCES

1 Shultz, et al. Humanized mice in translational biomedical research, Nat. Rev. Immunol. 7 (2007)
2 Heuts et al. Alloreactivity but failure to reject islet transplants by humanized BALB/c rag2gc mice. Scand J. Immunol. 71: 83-90, 2010
3 Watanabe et al. The analysis of the functions of human B and T cells in humanized NOD/shi-scid/gammanull (NOG) mice (hu-HSC-NOG). Int. Immunol. 21:843-58, 2009
4 Brehm et al. Parameters for establishing humanized mouse models to study human immunity: analysis of human hematopoietic stem cells engraftment in 3 immunodeficient strains of mice bearing the IL2Rgamma (null) mutation. Clin. Immunol. 135:84, 2010
5 Lent et al. IL-7 enhances thymic human T cell development in "human immune system" Rag2−/−IL2Rgammac−/− mice without affecting T cell homeostasis. J, Immunol. 183:7645-55, 2009
6 Jaiswal et al. Dengue Virus Infection and Virus-Specific HLA-A2 Restricted Immune Responses in Humanized NOD-scid IL2rcnull Mice. PLOS One 4:e7251, 2010
7 Ishikawa et al. Development of functional human blood and immune systems in NOD/SCID/IL2 receptor {gamma} chain (null) mice. Blood 106: 1565-1573, 2005
8 Sato et al. Dynamics of memory and naïve CD8+ T lymphocytes in humanized NOD/SCID/IL-2Rgammanull mice infected with CCR5-tropic HIV-1. Vaccine 28 suppl 2:B32-7, 2010
9 Kwant-Mitchell et al. Mucosal innate and adaptive immune responses against herpes simplex virus type 2 in a humanized mouse model. J, Virol. 83:10664-76, 2009.
10 Casares, S. & Brumeanu, T. D. Insights into the pathogenesis of type 1 Diabetes: a hint for novel immunospecific therapies. *Curr. Mol. Med.* 1:357-378, 2001.
11 Strowig T, Gurer C, Ploss A, Liu Y F et al. Priming of protective T cell responses against virus-induced tumors in mice with human immune system components. J Exp Med. 206(6):1423-34. (2009).
12 Shultz L D, Saito Y, Najima Y, Tanaka S. et al. Generation of functional human T-cell subsets with HLA-restricted immune responses in HLA class I expressing NOD/SCID/IL2r gamma (null) humanized mice. *Proc Natl Acad Sci USA*. 2010 Jul.

What is claimed is:

1. A transgenic NOD mouse whose genome comprises a nucleic acid construct comprising a nucleic acid encoding human leukocyte antigen DR4 (HLA-DR4) operably linked to mouse I-E$^d$ promoter, wherein the transgenic NOD mouse is homozygous for a null mutation in the RAG-1(Rag1$^{-/-}$) gene and null for the mouse interleukin 2 receptor gamma chain (IL-2Rγc) gene; and wherein the transgenic mouse expresses said HLA-DR4 and develops a functional human immune system comprising human T-cells, human B-cells and serum levels of human IgA, IgM, IgE and IgG, wherein said functional human immune system in said mouse is produced by infusion of human HLA-matched hematopoietic stem cells.

2. The transgenic mouse of claim 1, wherein genome of said transgenic mouse further comprising an expression vector comprising nucleic acid encoding human costimulatory molecules (CD80) operably linked to a rat insulin promoter (RIP).

* * * * *